United States Patent [19]

Lanier

[11] 4,384,000
[45] May 17, 1983

[54] METHOD FOR TREATMENT OF VARIOUS DERMATOLOGICAL CONDITIONS

[76] Inventor: Earl W. Lanier, 1107 Dunford Dr., St. Louis, Mo. 63137

[21] Appl. No.: 321,800

[22] Filed: Nov. 16, 1981

Related U.S. Application Data

[63] Continuation of Ser. No. 175,938, Aug. 7, 1980, abandoned, which is a continuation of Ser. No. 56,512, Jul. 11, 1979, abandoned, which is a continuation of Ser. No. 941,976, Sep. 13, 1978, abandoned, which is a continuation of Ser. No. 848,513, Nov. 4, 1977, abandoned, which is a continuation of Ser. No. 731,828, Oct. 12, 1976, abandoned, which is a continuation of Ser. No. 601,378, Aug. 4, 1975, abandoned.

[51] Int. Cl.$^3$ .......................................... A61K 31/445
[52] U.S. Cl. ..................................................... 424/267
[58] Field of Search ......................................... 424/267

[56] References Cited

U.S. PATENT DOCUMENTS 3,790,581  2/1947  Kreider .......................... 260/293.71

OTHER PUBLICATIONS

Cuhing, Handbook of Pharmacology, (1969), pp. 361 and 642.
Physicians Desk Reference, (PDR), 1974, pp. 1340–1341.
Janssen, Chemical Abstracts 71: 81194g, (1969).
Heykants et al., Chemical Abstracts 77: 83355h, (1972).

*Primary Examiner*—Leonard Schenkman
*Attorney, Agent, or Firm*—Kalish & Gilster

[57] ABSTRACT

The method for treatment of various cellular diseases and, more particularly, various dermatological conditions is comprised of administrating dosages of diphenoxylate hydrochloride either topically and/or systemically.

10 Claims, No Drawings

METHOD FOR TREATMENT OF VARIOUS DERMATOLOGICAL CONDITIONS

This application is a continuation of Ser. No. 175,938, filed Aug. 7, 1980, which is a continuation of Ser. No. 056,512, filed July 11, 1979, which is a continuation of Ser. No. 941,976, filed Sept. 13, 1978, which is a continuation of Ser. No. 848,513, filed Nov. 4, 1977, which is a continuation of Ser. No. 731,828, filed Oct. 12, 1976, which is a continuation of Ser. No. 601,378, filed Aug. 4, 1978, all now abandoned.

BACKGROUND AND SUMMARY OF THE INVENTION

This invention relates in general to cellular diseases in human beings and animals and, more particularly, to a method for treatment of certain dermatological conditions of the papulosquamous type wherein a thickening caused by an accumulation and overproduction of epithelial cells occurs, and those conditions of a generally inflammatory nature, or both.

The present invention resides in the administration of diphenoxylate hydrochloride for various cellular afflictions by reason of newly discovered modes of action of said compound. This particular compound and its method of preparation is set forth and described in U.S. Pat. No. 2,898,340 which issued Aug. 4, 1959 and wherein its efficacy in the treatment of diarrhea is noted by reason of its being a highly active inhibitor of gastro-intestinal propulsion and defecation. In about 1960 the combination of diphenoxylate hydrochloride with atropine sulfate was introduced to the market under the trademark LOMOTIL*. This preparation has been only recommended for the symptomatic treatment of diarrhea and gastro-intestinal disorders, being considered effective as adjunctive therapy in the management of diarrhea. Extensive use of this particular combination through the years has proven its safety and efficacy in treating said conditions with a relatively low incidence of adverse reaction. The subtherapeutic dose of atropine sulfate was added to make it practically impossible for extraction of the active principal for purposes of abuse**. The mode of action of diphenoxylate hydrochloride for the aforesaid purpose appears to be through increased intestinal tone and inhibition of gastro-intestinal motility. As indicated, the said compound for such purposes has been taken only systemically and with the unit dose being two tablets, or 5.0 mg. diphenoxylate hydrochloride, four times a day, that is, 20 mg. of diphenoxylate hydrochloride daily. Such dosage level will be required until control of the condition is effected and thereafter the dosage may be reduced for maintenance purposes.

*LOMOTIL is a registered trademark of Searle & Co. for tablets containing 2.5 mg. diphenoxylate hydrochloride and 0.025 mg. atropine sulfate, as well as for a liquid wherein each 5 ml. contains the aforesaid amounts of said ingredients.
**See Weingarten, B.; Weiss, J., and Simon, M.: "A Clinical Evaluation of a New Antidiarrheal Agent". Amer. Jour. Gastroent. 35:628-33, June 1961.

Accordingly, to the present time, the only utilization of diphenoxylate hydrochloride in human beings has been for diarrhea and gastro-intestinal dysfunctions.

Through extensive study and clinical testing, it has been discovered that certain skin diseases may be treated effectively with diphenoxylate hydrochloride by reason of hitherto unrecognized modes of action of said compound in human beings, as well as in animals. It has been demonstrated most lucidly that when utilized in various dermatological conditions, said compound has the capacity to suppress epithelial proliferation through cytotoxic growth-inhibitory and keratolytic effects on hyperplastic epidermal cells, as well as having anti-pruritic and anti-inflammatory properties. By virtue of these now discovered capacities of the aforesaid compound, the same has demonstrated marked effectiveness in the therapy of certain skin diseases comprehending many which had been to the present time substantially resistant to treatment or for which no specific treatment has been available.

Therefore, it is an object of the present invention to provide a method for treating skin diseases of the papulosquamous and inflammatory types by administering a currently available compound.

It is another object of the present invention to provide a method for the purpose above stated wherein the effective dosage of the particular compound may be administered topically or systemically, or orally, dependent upon the extent of the afflicted areas and desired therapeutic goals.

It is another object of the present invention to provide a method of the character stated which does not cause adverse side reactions upon the patient.

It is a still further object of the present invention to provide a method of the character stated wherein the compound administered is in dosages substantially less than that requisite for use of the compound for its heretofore known and accepted therapeutic purpose.

It is another object of the present invention to provide a method of the character stated which is useful with both adults and children, as well as with animals.

It is a further object of the present invention to provide a method of controlling and/or eliminating itching without respect to the physiologic basis for the same.

It is a still further object of the present invention to provide a method for treating various skin diseases as well as to alleviate symptoms thereof which may be practiced by the patient pursuant to appropriate dosage instructions and thereby obviating the necessity of professional administration.

DESCRIPTION OF THE INVENTION

This invention contemplates the administration of diphenoxylate hydrochloride to individuals suffering from papulosquamous and/or inflammatory dermatoses, as well as for producing anti-pruritic and anti-inflammatory effects. As will be discussed more fully hereinbelow, the said compound may be administered topically or systemically, as by orally ingestable tablets. The compound more popularly known as diphenoxylate hydrochloride is 2,2-diphenyl-4-(4'-carboxy-4'-phenyl-1'-piperidino) butyronitrile ether ester hydrochloride* whose structural formula is

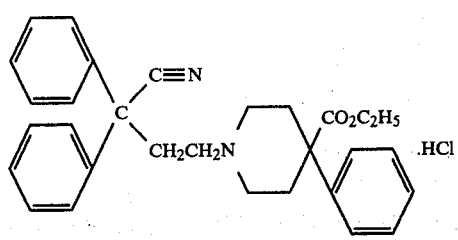

As developed hereinabove, to the present time the said compound had had usage in the pharmacological field only for the treatment of diarrhea and related gastro-intestinal conditions. The dermatological conditions treatable by administration of diphenoxylate hydrochloride comprehends many such conditions which to the present time have been generally resistant to other treatment regimens or for which there has been no known disease-specific treatment. Dermatological conditions which have been responsive to therapy with diphenoxylate hydrochloride include psoriasis, seborrheic dermatitis, pityriasis rosea, lichen planus, atopic dermatitis, eczematous dermatoses, pruritic conditions, ichthyosis, seborrheic keratosis and other hyperkeratoses, all of which will be more fully discussed in the examples hereinbelow.

*See U.S. Pat. No. 2,898,340

These aforesaid conditions may be efficaciously and safely treated with salutary effects by a topical method of application of diphenoxylate hydrochloride or by a systemic method of application. In those conditions wherein the diseased areas are relatively localized the topical application of the medication in an ointment, cream or lotion form is most adequate. Whereas when the area afflicted is of such extent as to be practically non-amenable to topical therapy then the systemic method is indicated. It should also be observed that if deemed advisable, both methods of application may be concurrently used or consecutively used and such modes of usage have caused enhanced effectiveness.

Diphenoxylate hydrochloride as heretofore used in the symptomatic treatment of gastro-intestinal conditions was administered in an individual dosage of 5.0 mg. taken internally four times daily. For the purpose of the present invention, the dosage for internal use or systemic application is approximately one-half of the customary dosage for gastro-intestinal symptom reduction purposes, that is, 2.5 mg. and with such dosages being taken two to three times daily. It will therefore be observed that the dosages of diphenoxylate hydrochloride for treatment of the aforesaid dermatological conditions is of such limited amount as to be non-productive of any adverse reactions which would necessitate discontinuance of therapy and to cause minimal inhibition of gastro-intestinal motility and defecation. For systemic application purpose, either the tablets of 2.5 mg. diphenoxylate hydrochloride or 5.0 ml. of the diphenoxylate hydrochloride liquid preparation may be used; while topical preparations can be compounded by making a smooth paste of the diphenoxylate hydrochloride tablets with the minimal quantity of distilled water, and then incorporating such paste within a selected vehicle for localized dermal application, as either in ointment, cream, or lotion form. Satisfactory objective and subjective symptomatic effects have been obtained applying the topical preparations from one to three times a day in responsive dermatological conditions. However, for symptomatic relief of pruritus or itching, patients have been permitted to apply the topical applications as often as necessary.

Topical preparations containing 0.125, 0.25 and 0.50 percent by weight of diphenoxylate hydrochloride have demonstrated the beneficial effects of dephenoxylate in responsive dermatological conditions. A suitable vehicle for providing diphenoxylate hydrochloric in a vanishing cream base is UNIBASE, a trademark of Parke Davis & Company for a preparation composed of cetyl alcohol, stearyl alcohol, petrolatum, glycerine, sodium lauryl sulfate, sodium citrate, propylparaben and water. Another suitable vehicle for providing diphenoxylate hydrochloride in an ointment base is EUCERIN, a trademark of Duke Laboratories to identify a preparation comprised of 50 percent Aquaphor* in a cholesterolized ointment base and 50 percent water. A lotion containing dephenoxylate hydrochloride may be made using as the vehicle LUBRIDERM, a trademark of Texas Pharmacal for a lotion containing oxycholesterin, mineral oil, sorbitol, cetyl alcohol, triethanolamine stearate, steric acid, paraben esters and purified water. The foregoing vehicles are merely exemplary of the numerous compositions which would be equally suitable for use with dephenoxylate hydrochloride, but are recited to demonstrate the ready availability of such bases. There are manifestly numerous absorbent ointment bases which may be used with equal effectiveness as vehicles for the preparation among which are those identified by the trademark POLYSORB (Fougera); QUAIATUM (Schieffelin); and VELVACHOL (Texas Pharmacal Company), also there are any number of emulsion ointment bases which are suitable. Bases of this class are either water-in-oil or oil-in-water emulsions. The oleaginous phase may contain petrolatum, fats, organic alcohols, or other grease-like substances. Both types of bases are insoluble in water but will take it up. The water-in-oil type (eg. lanolin) is difficult to wash off, whereas the oil-in-water type (eg. hydrophilic ointment, so-called vanishing creams) washes off fairly readily.

*Aquaphor is a trademark of Duke Laboratories for an absorbent ointment base.

Hydrophilic ointment contains white petrolatum, stearyl alcohol, and propylene glycol in water along with emulsifying agents and preservatives; it is a good vehicle for water-soluble medicaments. It has good esthetic properties and its texture imparts a pleasant sensation to the skin.

Cold cream is a water-in-mineral oil emulsion (absorption base) that also contains white wax, spermaceti, and sodium borate. It has lubricating qualities, provides some water for hydration of the epidermis, is an excellent vehicle for the incorporation of many medicaments, and has some cooling activity. Cold creams similar to the above formulation are widely used as vehicles. Preparations conforming to the above are as follows, being identified by trademark: ACID MANTLE (Dome Laboratories) for use as a cream or lotion; CETAPHIL (Texas Pharmacal Company) for use as a cream or lotion; EMULSION BASE (Schieffelin) for use as an emulsion ointment base; NEO BASE (Burroughs Wellcome Company) for use as an ointment base; NIVEA (Duke) for use as a cream.

Determination of the percentage of diphenoxylate hydrochloride to be incorporated with the appropriate vehicle is dependent on the clinical judgment of the physician for the specific dermatological condition being treated. However, with all conditions the 0.5% topical preparation has proved efficacious, however, for the sake of economy it is preferable to use the lowest effective percentage. In general the lowest percentage composition of diphenoxylate hydrochloride which proves effective in a specific case is the proper concentration which should be used. Selection of the appropriate vehicle for specific patients is again dependent on the clinical judgment of the prescribing physician who will consider the factors of patient acceptance and compliance, status of the disease and therapeutic goals. In general, lotion preparations are amenable to treating widespread mild dermatological conditions due to the ease and efficacy of application; vanishing cream preparations are appropriate for all responsive dermatological conditions and are practically universally accepted because of the esthetic nature of these vehicles; ointment preparations are most efficient for treating chronic thickened localized areas of dermatitis because of the longer therapeutic action obtained with these preparations; suppository preparations comprising a cocoa butter base having one half percent by weight of diphenoxylate hydrochloride mixed therein may be used for the specific affliction of proctitis; shampoo preparations having mixed therein one half percent by weight of diphenoxylate hydrochloride are suitable for treating hairy areas including the effective control of dandruff; and the diphenoxylate hydrochloride may be incorporated in aerosol preparations for alleviation in the treatment of sensitive areas. Since ointment vehicles have a longer duration, a lower concentration of diphenoxylate hydrochloride may be used for as effective a response as may be obtained from the use of the same in a cream or lotion base.

The indications, dosages, methods of use and modes of action for diphenoxylate hydrochloride which constitute this invention will appear more fully from consideration of the hereinbelow examples which are given for the purpose of illustration only and are not to be construed as limiting the invention in spirit or in scope. The examples will more readily reveal the efficacy of the present method in treating various skin diseases with the same constituting selected clinical cases which are representative of results obtained for the particular affliction discussed.

EXAMPLE I

Psoriasis

This Papulosquamous Inflammatory Dermatosis has shown objectively favorable response to systemic and/or topical therapy with diphenoxylate hydrochloride. Ordinarily therapy of Psoriasis is primarily limited to a great variety of topical measures. The only systemic medication that is currently cautiously recommended by the American Medical Association for the symptomatic control of severe, recalcitrant disabling Psoriasis is the antimetabolite METHOTREXATE, a trademark of Lederle Laboratories.

CASE 1: ACUTE PSORIASIS GUTTATE of three weeks duration in a 12 year old white female had complete remission free of adverse effects within 29 days of systemic diphenoxylate hydrochloride therapy. Initial dosage was 2.5 mg. diphenoxylate hydrochloride twice a day for four days. Subsequent dosage was increased to 2.5 mg. three times a day until all psoriatic lesions had disappeared. This patient had no recurrence after more than a year since her acute attack.

CASE 2: CHRONIC PSORIASIS of 22 years duration involved the knees and elbows of a 62 year old white female and demonstrated the effectiveness of both systemic and topical diphenoxylate hydrochloride therapy. This patient participated in a double-blind cross-over study of six weeks duration using a 0.50 percent by weight diphenoxylate hydrochloride preparation in a vanishing cream base and a similar placebo preparation which differed only in not containing any diphenoxylate hydrochloride. She had a similarly objectively favorable response to a 42 day course of systemic therapy which consisted of taking 2.5 mg. diphenoxylate hydrochloride three times a day. During the course of systemic treatment she reported mild constipation and nausea. Currently this patient is responding well and progressively to maintenance therapy using the 0.25 percent by weight diphenoxylate hydrochloride ointment preparation twice daily and as needed if itching recurs.

CASE 3: CHRONIC PUSTULAR PSORIASIS of 12 years duration involved the soles of a 56 year old white female and had been resistant to previous systemic and topical therapies which had included the hereinabove mentioned METHOTREXATE. This patient participated in a bilateral comparison control study of two weeks duration which demonstrated the efficacy of the 0.50 percent by weight diphenoxylate hydrochloride vanishing cream preparation applied twice daily. She had progressive improvement for the next 56 days with the same preparation applied to both feet twice daily and no longer experienced any itching although pustules were still present. The same topical treatment was continued and additional systemic therapy with 2.5 mg. of diphenoxylate hydrochloride taken orally three times a day was instituted for the next 63 days with no adverse effects and complete remission of the pustular psoriasis. She has had no recurrence in more than six months using the topical diphenoxylate hydrochloride cream as needed for maintenance therapy.

CASE 4: CHRONIC PSORIASIS of 38 years duration involved the elbows of a 61 year old white female and responded within 14 days to the topical application of the 0.50 percent by weight diphenoxylate hydrochloride vanishing cream three times a day. Remission is being maintained with the 0.25 percent by weight diphenoxylate hydrochloride ointment applied two to three times a day the past three months.

EXAMPLE II

Seborrheic Dermatitis

These Papulosquamous Inflammatory Dermatoses of chronic character are of undetermined etiology and characterized by mild to moderate itching, dry, moist or greasy scales and spontaneous remissions and exacerbations. The anti-pruritic, anti-inflammatory and epithelial suppressive actions of diphenoxylate hydrochloride were demonstrated with both systemic and topical therapy. Systemic therapy, consisting of 2.5 mg. diphenoxylate hydrochloride taken orally three times daily, for one to four weeks relieved itching, dandruff, and blotching of the face. Topical therapy, consisting of the 0.25 or 0.50 percent by weight diphenoxylate hydrochloride vanishing cream preparation applied one to three times daily, relieved itching almost immediately and resolved the dermatitis after about 14 days. Seborrheic involvement of the nasolabial, glabellar and aural regions responded the quickest to topical treatment.

CASE 5: LICHENOID SEBORRHEIC DERMATITIS of many years duration involved the midscapular region of a 58 year old white male was the slowest to completely respond to diphenoxylate hydrochloride therapy. He had almost immediate relief of the itching and a gradual decrease in the thickness of the involved skin with the twice daily application of the 0.25 percent by weight diphenoxylate hydrochloride vanishing cream preparation over a period of 84 days. After said topical regimen, a systemic regimen of 67 days was commenced because there was still some hyperemia (redness) in the midscapular region, and he had developed extension seborrheic involvement of his anterior chest; said dosage being 2.5 mg. diphenoxylate hydrochloride orally three times a day. Improvement of his back and chest was apparent by the 16th day and complete healing had occurred by the 67th day.

CASE 6: CHRONIC SEBORRHEIC DERMATITIS of several years duration involving the ears and midscapular area of the back of a 54 year old white female was treated by applying the 0.50 percent by weight diphenoxylate hydrochloride vanishing cream preparation three times a day. After three days of treatment, she obtained relief from the itching of her ears concommitant with a softening of the area on her back. Marked improvement of the dermatitis in both ears and back was apparent by the 11th day.

EXAMPLE III

Pityriasis Rosea

A Primary Dermatosis of the Papulosquamous Inflammatory Group of unknown etiology which is characterized by the appearance of oval scaly maculat lesions which spontaneously regress in six weeks or longer. Prior to the present invention there has been no known specific treatment of Pityriasis Rosea which would shorten its natural course of six weeks.

CASE 7: PITYRIASIS ROSEA of 10 days duration in a 61 year old white female had complete remission free of adverse effects after 24 days of using 2.5 mg. diphenoxylate hydrochloride orally three times a day. Within seven days of initiation of therapy there was obvious evidence of the epithelial suppressive effect of diphenoxylate hydrochloride in that the original lesions manifested central clearing and the most recently developing lesions were smaller and less scaly. By the 14th day these latter lesions were regressing and no new lesions were developing.

CASE 8: PITYRIASIS ROSEA of 10 days duration in a 22 year old white male had complete remission free of adverse effect with 14 days of the systemic therapy as described in Case 7 hereinabove.

CASE 9: PITYRIASIS ROSEA of four days duration in an 11 year old white male had complete remission free of adverse effect with seven days of the systemic therapy as described in Case 7 hereinabove.

EXAMPLE IV

Lichen Planus

This Papulosquamous Inflammatory Dermatosis of unknown etiology is persistent and recalcitrant to treatment when it occurs in adults and has a tendency to relapse. The suppressive effect of diphenoxylate hydrochloride on proliferative epithelial cells without injury to adjacent normal skin was demonstrated with both topical and systemic therapy.

CASE 10: HYPERTROPHIC LICHEN PLANUS of many years duration on the tibial surface of the left leg of a 72 year old white female was regressing within nine days after applying the 0.50 percent by weight diphenoxylate hydrochloride vanishing cream preparation three times a day.

CASE 11: HYPERTROPHIC LICHEN PLANUS of unknown duration involved the sternal region of a 93 year old white female. This patient had a regression of the lesion free of adverse effect after 15 days of therapy with 2.5 mg. diphenoxylate hydrochloride orally three times a day which said regression was still continuing two months after the initiation of therapy.

EXAMPLE V

Atopic Dermatitis

This is an Eczematous Inflammatory Dermatitis of a basically hereditary diathesis of excessive cutaneous reactivity to many different irritants. Diphenoxylate hydrochloride therapy has been beneficial in relieving the combination of intense pruritus and eczematoid skin eruptions in the adolescent phase of atopic dermatitis.

CASE 12: ATOPIC DERMATITIS of eight years duration involved the antecubital fossae and forehead of a 13 year old white female. A nummular exzematous lesion of three weeks duration involved her left cheek. Complete regression of all lesions were obtained by using the 0.50 percent by weight diphenoxylate hydrochloride vanishing cream preparation three times a day for six weeks and then the ointment preparation three times a day the next four weeks.

CASE 13: ADOLESCENT ATOPIC DERMATITIS of many years duration and widespread involvement in an 18 year old white female demonstrated the efficacy of concomitant systemic and topical diphenoxylate hydrochloride free of adverse effects. Some improvement was apparent after using the 0.50 percent by weight diphenoxylate hydrochloride vanishing cream preparation twice a day for 14 days. More dramatic improvement was obtained the next 14 days using concomitant therapy of the 0.25 percent by weight vanishing cream preparation twice a day and 2.5 mg. diphenoxylate hydrochloride orally three times a day.

EXAMPLE VI

Eczematous Dermatoses

Eczema is a term applied to lesions of Inflammatory Dermatoses of diverse etiology and pathogenesis. The same is characterized by superficial inflammation with a mixture of erythema, exudation, vesiculazation and edema with oozing, crusting and scaling. Itching, especially at night, is a fairly consistent hallmark of eczema. Diphenoxylate hydrochloride therapy has relieved subacute, acute and chronic eczematous dermatitis.

CASE 14: CHRONIC RECURRING NEURODERMATITIS had been involving the right hand of a 58 year old white female for years. Using the 0.25 percent by weight diphenoxylate hydrochloride vanishing cream preparation three times a day relieved the itching after the third or fourth application and the hand was softer within two weeks of therapy. Regression of the dermatitis has been maintained for more than a year with the occasional application of the medication.

CASE 15: ALLERGIC CONTACT SENSITIZATION DERMATITIS of four days duration involving the right wrist and left antecubital region in a 50 year old white female began to extend to the trunk and was more pruritic by the fifth day of standard systemic corticosteroid and specific antigen therapy. Systemic diphenoxylate hydrochloride therapy, 2.5 mg. three times a day for three days, showed an initial response with decreased induration within two days and complete healing of the involved areas by the fifth day.

CASE 16: LOCALIZED NONSPECIFIC ECZEMATOUS DERMATITIS of over a month's duration involved the posterior distal aspect of the right leg in a 17 year old white female. Additionally, she had dry pruritic upper and lower extremities with erythema of the dorsum of her hands. After nine days of diphenoxylate hydrochloride topical therapy with the 0.50 percent by weight preparation applied three times a day to the eczematous areas, and as needed for itching in the other regions, the pruritus was relieved and the eczema was involuting. Marked improvement was apparent after 20 days of topical diphenoxylate hydrochloride therapy and regular use was able to be discontinued.

CASE 17: VARICOSE STASIS DERMATITIS with a history of recurrence for more than eleven years involved the distal lateral aspect of the left leg in a 69 years old white female. The eczematous area was practically healed within a week of using the 0.50 percent by weight diphenoxylate hydrochloride vanishing cream preparation twice a day and as needed for itching. The 0.25 percent by weight vanishing cream preparation was equally effective a month later with recurrence of the eczema. No further recurrence has occurred.

CASE 18: CHRONIC CONTACT DERMATITIS (Housewife's Eczema) of over five years duration involving both hands of a 35 year old white female responded favorably to both systemic and topical diphenoxylate hydrochloride therapy. A 10 day course of 2.5 mg. diphenozylate hydrochloride orally three times a day improved her hands an estimated 50 percent. A 14 day course of the 0.50 percent by weight diphenoxylate hydrochloride vanishing cream preparation was reported to have relieved the itching and cleared the dermatitis within a week and was considered superior to any therapy previously used. Her improved status has been maintained for more than seven months with the occasional use of the topical preparation.

CASE 19: CHRONIC SUBACUTE ECZEMA of many years duration with dryness and cracking of the fingertips of a 54 year old white female improved within three days of using the 0.25 percent by weight diphenoxylate hydrochloride ointment preparation twice a day.

EXAMPLE VII

Pruritus With and Without Dermatitis

Pruritus is a sensation exclusive to the skin, the most common symptom of dermatological diseases and additionally is a symptom in numerous internal disorders. The anti-pruritic effect of diphenoxylate hydrochloride has been shown in numerous of the preceding examples and is further demonstrated in the following:

CASE 20: CHRONIC PRURITIC DERMATITIS of many months duration involving the distal medial aspect of the right leg of an 86 year old white male completely regressed with the twice daily application of the 0.50 percent by weight diphenoxylate hydrochloride vanishing cream preparation. Itching was reported to have ceased with the first application and no visible dermatitis could be detected when the patient was examined six weeks later.

CASE 21: PRURITUS VULVAE AND ANTECUBITAE of recent origin in a 65 year old white female responded within a week of topically applying the 0.50 percent by weight diphenoxylate hydrochloride vanishing cream preparation as often as needed to relieve the itching.

CASE 22: PRURITUS SCROTI of six to eight months duration in a 73 year old white male was relieved within 13 days of topically using the 0.25 percent by weight diphenoxylate hydrochloride vanishing cream preparation twice daily.

CASE 23: PRURITUS ANI with adjacent inflammatory induration of a month's duration in a 55 year old white male completely cleared with applying the 0.50 percent by weight diphenoxylate hydrochloride vanishing cream preparation three times a day. The itching ceased during the first day of therapy and the inflammatory induration gradually decreased in area and thickness until complete healing occurred at about two months.

CASE 24: PRURITUS WITHOUT DERMATITIS had repeatedly involved the left cheek of a 55 year old white female and topical application of the 0.25 percent by weight diphenoxylate hydrochloride vanishing cream preparation was reported by the patient to have relieved the itching better than the previously used topical corticosteroid preparations.

EXAMPLE VIII

ICHTHYOSIS

This particular disease is characterized by dryness and scaliness of the skin, the result of a congenital dysplasia of keratinization and for which therapy has been nonspecific. Both mild and severe forms of ichthyosis and ichthyosiform dermatoses have shown efficacious and safe responses to specific therapy with diphenoxylate hydrochloride over extended periods. An intricable portion of the present invention is the newly found specific cytotoxic effect of diphenoxylate hydrochloride on hyperplastic epithelial cells and was best demonstrated by the lifting and shedding of the scales in the cases of ichthyosis.

CASE 25: ICHTHYOSIS VULGARIS since birth in a 21 year old white male had a satisfactory remission to a 66 day course of 2.5 mg. diphenoxylate hydrochloride orally three times a day which persisted for another 109 days after (therapy without recurrence). Favorable progression of response free of adverse effects to a second course of 2.5 mg. diphenoxylate hydrochloride orally three times a day has past the 150th day of therapy.

CASE 26: ICHTHYOSIS CONGENITA of lifelong duration in a 69 year old white male had a remission of his generalized condition to 110 days of systemic diphenoxylate hydrochloride therapy that was still satisfactory eight months later. He was treated with 2.5 mg of the medication three times a day for 84 days when this was decreased to twice a day because he could no longer distinguish that he was shedding skin. By the 12th day of therapy the hyperkeratotic skin over his elbows improved sufficiently to enable him to fold this skin thereover for apparently the first time in his life.

CASE 27: ICHTHYOSIS CONGENITA of a mild degree in a 54 year old white male had a clinically complete remission to a 33 day course of 2.5 mg. dipehnoxylate hydrochloride orally three times a day that lasted for more than six months. Subsequently he has similarly favorably responded to the 0.50 and 0.25 percent by weight diphenoxylate hydrochloride vanishing cream and the 0.125 percent by weight diphenoxylate hydrochloride lotion preparations applied locally twice a day and as needed to relieve itching.

CASE 28: ICHTHYOSIFORM DERMATITIS which consisted of extreme dryness of her hands along with cracking of the fingertips for as long as she could remember in a 57 year old white female completely responded within a few days to applying the 0.125 percent by weight dipehnoxylate hydrochloride ointment preparation twice a day.

EXAMPLE IX

SEBORRHEIC KERATOSIS

This term designates a hyperplastic epidermal condition which is usually resistant to all but destructive therapeutic measures. An intricable portion of the present invention is the newly found specific keratolytic effect of diphenoxylate hydrochloride or hyperplastic epithelium without injury to adjacent normal skin or adverse systemic action and was most graphically seen in the melting away of the kerototic lesions with no evidence of residual scar formation.

CASE 29: NEVOID SEBORRHEIC HYPERKERATOSIS of a few weeks duration on the back of the left hand of a 57 year old white female clinically exhibited essentially no response to applying the 0.25 percent by weight diphenoxylate hydrochloride vanishing cream preparation three times a day for 28 days. However, with a 14 day course of 2.5 mg. diphenoxylate hydrochloride orally three times a day the lesion began regressing in eight days and had completely vanished three days after the course of therapy had been completed.

CASE 30: HORNY SENILE KERATOSIS of six months duration on the left side of the scalp in an 86 year old white male had an 85 percent reduction in size following 65 days of applying the 0.50 percent by weight diphenoxylate hydrochloride vanishing cream preparation twice daily. Within three weeks of commencing therapy liquefaction of the horny lesion without irritation of the surrounding normal tissue was observed.

CASE 31: VERRUCOUS SENILE KERATOSES of more than a year's duration involved the temporal regions of a 74 year old white male had flattening of both lesions with about 80 percent healing following 62 days of applying the 0.50 percent by weight diphenoxylate hydrochloride vanishing cream preparation one to three times a day and concomitantly taking 2.5 mg. diphenoxylate hydrochloride orally twice a day for the last 33 days of the treatment period. Marked improvement with dry regression of the lesions was observed on the seventh day of therapy. Further improvement progressively continued throughout, and after, the course of therapy without any adverse effects.

CASE 32: SEBORRHEIC HYPERKERATOSES involving two small areas on the right side of the scalp in a 55 year old white female had been unresponsive to the three times a day application of a corticosteroid ointment preparation for a month. After applying the 0.50 percent by weight diphenoxylate hydrochloride vanishing cream preparation three times a day for 14 days the lesions had decreased by 50 percent. Therapy was continued for three months until the lesions were healed.

EXAMPLE X

HYPERKERATOSIS

This is another hyperplastic epidermal condition being a common pathologic condition of either primary or secondary occurrence, with increased thickening or hypertrophy of the uppermost layer of the skin, the stratum corneum. It is an intensification of the normal process of cornification due to hereditary disposition, to increased pressure or to irritation. Therapy with diphenoxylate hydrochloride has been effective in relieving hyperkeratosis of varying etiologies.

CASE 33: CHRONIC RADIODERMATITIS of seven years duration with pruritic brownish thicken areas involving the thyroid region of the neck in a 65 year old white male cleared within 14 days of using the 0.50 percent by weight diphenoxylate hydrochloride vanishing cream preparation locally twice a day.

CASE 34: HYPERKERATOSIS PLANTARIS of many years duration involving the soles of a 52 year old white female responded the best compared to numerous previous therapeutic regimens when topical diphenoxylate hydrochloride therapy was used. The 0.50 percent by weight vanishing cream preparation was applied three times a day for six weeks with healing of cracked areas. The next six weeks the 0.50 percent by weight ointment preparation was applied twice a day resulting in complete resolution of the hyperkeratosis.

CASE 35: CALLUS of the ball of the right foot in a 68 year old white male vanished with the twice daily application of the 0.50 percent by weight diphenoxylate hydrochloride ointment preparation of eight weeks.

The overall clinical results obtained in responsive dermatological conditions proved to be quite similar in efficacy for either topical or systemic diphenoxylate hydrochloride therapy. The average range in days of therapy when an initial favorable response was observed in the various responsive dermatological conditions was 7.9 to 29.5 days with topical therapy and 8.2 to 28.9 days with systemic therapy. The efficacy of diphenoxylate hydrochloride therapy as above described was at least 72.4 percent with respect to results that could be classified as excellent to good. The clinical safety of topical therapy was 100 percent, there being no adverse side effects; while with systemic therapy there were no adverse side effects in 72.9 percent of the cases, and such side effects as may have been experienced in the remaining cases were not necessarily as a result of the therapy.

Having described my invention, what I claim and desire to obtain by Letters Patent is:

1. The method of treating human dermatological conditions selected from the class consisting of papulosquamous inflammatory dermatoses, inflammatory dermatoses, pruritus, ichthyosis, and hyperplastic epidermal conditions comprising the administration of an effective dosage of diphenoxylate hydrochloride to a patient suffering therefrom.

2. The method of treating human dermatological conditions as defined in claim 1 wherein said diphenoxylate hydrochloride is administered topically to the afflicted area.

3. The method of treating human dermatological conditions as defined in claim 2 wherein said diphenoxylate hydrochloride is in a preparation wherein said diphenoxylate hydrochloride constitutes between 0.125 and 0.5 percent by weight thereof and the balance being compatible lotion base, ointment base, emulsion, or cream base.

4. The method of treating human dermatological conditions as defined in claim 3 wherein said diphenoxylate hydrochloride preparation is applied topically at least twice diurnally until the particular condition is alleviated.

5. The method of treating human dermatological conditions as defined in claim 1 wherein the diphenoxylate hydrochloride is administered systematically.

6. The method of treating human dermatological conditions as defined in claim 5 wherein the diphenoxylate hydrochloride is administered in a dosage of 2.5 mg.

in at least two dosages diurnally until the condition is alleviated.

7. The method of treating human dermatological conditions as defined in claim 6 wherein said dosages are in tablet form.

8. The method of treating human dermatological conditions as defined in claim 1 wherein the diphenoxylate hydrochloride is administered concurrently both topically and systemically.

9. The method of treating human dermatological conditions as defined in claim 8 wherein the diphenoxylate hydrochloride is administered topically in a preparation comprising between 0.125 to 0.5 percent by weight of diphenoxylate hydrochloride and the balance being a compatible lotion base, ointment base, emulsion base, or cream base, and the diphenoxylate hydrochloride being administered systematically being in tablet form constituting 2.5 mg. thereof.

10. The method of treating human dermatological conditions as defined in claim 9 wherein the topical preparation of diphenoxylate hydrochloride is applied at least twice daily and the systemic tablet is administered at least twice daily until the particular condition is alleviated.

* * * * *